United States Patent
Klimowski et al.

(12) 
(10) Patent No.: US 6,489,448 B1
(45) Date of Patent: Dec. 3, 2002

(54) ANTIPARASITIC HELMINTH LARVAL THIOL SPECIFIC ANTIOXIDANT-ANTIBODIES, AND USES THEREOF

(75) Inventors: Laura Klimowski, Ft. Collins, CO (US); Cynthia Ann Tripp, Ft. Collins, CO (US)

(73) Assignee: Heska Corporation, Ft. Collins, CO (US)

( * ) Notice: Subject to any disclaimer, the term of this patent is extended or adjusted under 35 U.S.C. 154(b) by 0 days.

(21) Appl. No.: 09/477,510

(22) Filed: Jan. 4, 2000

Related U.S. Application Data

(62) Division of application No. 09/004,716, filed on Jan. 7, 1998, now Pat. No. 6,031,077, which is a division of application No. 08/602,262, filed on Feb. 15, 1996, now Pat. No. 5,744,593.

(51) Int. Cl.[7] ............... C07K 16/00; A61K 39/395; A61K 39/40; C12P 21/08; C07H 21/04
(52) U.S. Cl. ............... 530/387.1; 530/388.1; 530/387.9; 530/388.2; 530/388.6; 530/389.1; 536/23.1; 536/23.4; 424/130.1; 424/136.1; 424/139.1; 424/151.1; 514/2
(58) Field of Search ............ 530/387.1, 388.1, 530/387.9, 388.2, 388.6, 389.1; 424/130.1, 136.1, 139.1, 151.1; 536/23.1, 23.4; 514/2

(56) References Cited

U.S. PATENT DOCUMENTS

| | | | |
|---|---|---|---|
| 4,568,639 A | | 2/1986 | Lew ............ 435/68 |
| 5,569,603 A | | 10/1996 | Tripp et al. |
| 5,632,991 A | * | 5/1997 | Gimbrone et al. |
| 5,639,876 A | * | 6/1997 | Tripp et al. |
| 5,681,724 A | | 10/1997 | Tripp et al. ......... 435/70.1 |
| 5,744,593 A | * | 4/1998 | Klimowski et al. |
| 5,750,391 A | * | 5/1998 | Tripp et al. |
| 5,863,775 A | * | 1/1999 | Atkinson et al. ....... 424/94.1 |
| 5,912,337 A | * | 6/1999 | Tripp et al. |
| 5,977,306 A | * | 11/1999 | Grieve et al. |
| 6,031,077 A | * | 2/2000 | Klimowski et al. |
| 6,060,281 A | * | 5/2000 | Grieve et al. |
| 6,114,142 A | * | 9/2000 | Grieve et al. |
| 6,150,135 A | * | 11/2000 | Chandrashekar et al. 435/235.1 |
| 6,159,500 A | * | 12/2000 | Demopoulos et al. |
| 6,207,158 B1 | * | 3/2001 | Tripp et al. |

FOREIGN PATENT DOCUMENTS

| | | |
|---|---|---|
| GB | 2152510 | 8/1985 |
| WO | 9415593 | 7/1994 |
| WO | 9524198 | 9/1995 |
| WO | 9637218 | 11/1996 |
| WO | 9640884 | 12/1996 |
| WO | WO97/29766 | * 8/1997 |

OTHER PUBLICATIONS

Abraham et al J. Parasilology 77/2: 254–257, 1991.*
Schrum et al, Molecular & Biochemical Parasitology 94:131–135, 1998.*
Klimowski et al, Molecular & Biochemistry Parasitology 90:297–306, 1997.*
Lu et al, Molecular & Biochemistry Parasitology 91:221–235, 1998.*
Grieve et al, J. Immunology, 148/8: 2511–2515, 1992.*
Blaxter et al., 1996, Genbank ANH39434.
Blaxter et al., 1996, Genbank ANR95325.
Bruchhaus et al., 1993, *Trop. Med. Parasitol.*, 44:116–118.
Chae et al., 1993, *J. Biol. Chem.*, 268(22):16815–16821.
Chae et al., 1994, *Proc. Natl. Acad. Sci. USA*, 91:7022–7026.
Chae et al., 1994, *Biofactors*, 4(3/4):177–180.
Chae et al., 1994, *Proc. Natl. Acad. Sci. USA*, 91:7017–7021.
Ghosh et al., 1995, *Am. J. Trop. Med. Hyg.*, 53(2)(Supp.):197 (Abstr. #332).
Ishii et al., 1993, *J. Biol. Chem.*, 268(25):18633–18636.
Kawai et al., 1994, *J. Biochem.*, 115:641–643.
Kim et al., 1988, *J. Biol. Chem.*, 263(10):4704–4711.
Lim et al., 1994, *Gene*, 140:279–284.
Prosperi et al., 1993, *J. Biol. Chem.*, 268(15):11050–11056.
Raghavan et al., 1995, *Am. J. Trop. Med. Hyg.*, 53(2)(Supp):196 (Abstr.).
Rasmussen et al., 1992, *Electrophoresis*, 13:960–969.
Reed et al., 1992, *Infect. Immun.*, 60(2):542–549.
Scott et al., 1995, *Am. J. Trop. Med. Hyg.*, 53(2)(Supp.):196 (Abstr. #330).
Torian et al., 1990, *Proc. Natl. Acad. Sci. USA*, 87:6358–6362.
Yamamoto et al., 1989, *Gene*, 80:337–343.

\* cited by examiner

*Primary Examiner*—Nita Minnifield
(74) *Attorney, Agent, or Firm*—Sheridan Ross P.C.

(57) ABSTRACT

The present invention relates to parasitic helminth thiol specific antioxidant (TSA) larval proteins; to parasitic helminth larval TSA nucleic acid molecules, including those that encode such TSA proteins; to antibodies raised against such TSA proteins; and to compounds that inhibit parasitic helminth larval TSA activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic helminths.

11 Claims, No Drawings

ANTIPARASITIC HELMINTH LARVAL THIOL SPECIFIC ANTIOXIDANT-ANTIBODIES, AND USES THEREOF

This Application is a Divisional Application of application Ser. No. 09/004,716, filed Jan. 7, 1998, which issued as U.S. Pat. No. 6,031,077, which is a Divisional of application Ser. No. 08/602,262, filed Feb. 15, 1996, and which issued as U.S. Pat. No. 5,744,593 on Apr. 28, 1998, entitled PARASITIC HELMINTH LARVAL THIOL SPECIFIC ANTIOXIDANT PROTEINS AND NUCLEIC ACID MOLECULES" each of which is incorporated herein by this reference in its entirety.

FIELD OF THE INVENTION

The present invention relates to parasitic helminth thiol specific antioxidant (TSA) nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or inhibitors, as well as their use to protect animals from diseases caused by parasitic helminths, such as heartworm.

BACKGROUND OF THE INVENTION

Parasitic helminth infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

An alternative method to prevent parasitic helminth infection includes administering a vaccine against a parasitic helminth. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of prominent antigens have been identified in several parasitic helminths, including in Dirofilaria, there is yet to be a commercially available vaccine developed for any parasitic helminth.

As an example of the complexity of parasitic helminths, the life cycle of *D. immitis*, the helminth that causes heartworm, includes a variety of life forms, each of which presents different targets, and challenges, for immunization. In a mosquito, *D. immitis* microfilariae go through two larval stages (L1 and L2) and become mature third stage larvae (L3), which can then be transmitted back to the dog. In a dog, the L3 molt to the fourth larval stage (L4), and subsequently to the fifth stage, or immature adults. The immature adults migrate to the heart and pulmonary arteries, where they mature to adult heartworms. Adult heartworms are quite large and preferentially inhabit the heart and pulmonary arteries of an animal. Sexually mature adults, after mating, produce microfilariae which traverse capillary beds and circulate in the vascular system of the dog.

In particular, heartworm is a major problem in dogs, which typically cannot even develop immunity upon infection (i.e., dogs can become reinfected even after being cured by chemotherapy), and is becoming increasingly widespread in other companion animals, such as cats and ferrets. Heartworm infections have also been reported in humans.

Prior investigators have identified yeast thiol specific antioxidants (TSAs), as well as cloning several mammalian TSA genes, a protozoan TSA gene and a partial nucleic acid sequence of an adult Onchocerca TSA gene; see, for example, Chandrashekar et al., Genbank Accession No. U09385; Yamamoto et al, 1989, *Gene* 80, 337–343, Torian et al., 1990, *Proc. Natl. Acad. Sci. USA* 87, 6358–6362, Reed et al., 1992, *Infection and Immunity.* 60, 542–549, Ramussen et al, 1992, *Electrophoresis* 13, 960–969, Tannich et al., 1993, *Trop. Med. Parasitol.* 44, 116–118, Prosperi et al., 1993, *J. Biol. Chem.* 268, 11050–11056, Ishii et al., 1993, *J. Biol. Chem.* 268, 18633–18636, Chae et al., 1993, *J. Biol. Chem.* 268, 16815–16821, Ishii et al., 1993, *J. Biol. Chem.* 268, 18633–18636, Chae et al., 1994, *Proc. Natl. Acad. Sci. USA* 91, 7022–7026, Kawai et al, 1994, *J. Biochem.* 115, 641–643, Chae et al, 1994, *Proc. Natl. Acad. Sci. USA* 91, 7017–7021 and Chae et al, 1994, *Biofactors* 4, 177–180. Although yeast, human and bovine cortex TSAs has been shown to have thiol-dependent reductase activity (see, for example, Sauri et al, 1995, *Biochem. Biophys. Res. Comm.* 208, 964–969; Watabe et al, 1995, *Biochem. Biophys. Res. Comm.* 213, 1010–1016), the other TSA genes having been identified by nucleic acid sequence homology. The determination of these sequences, however, does not indicate or suggest the cloning of novel larval parasitic helminth TSA genes.

As such, there remains a need to identify an efficacious composition that protects animals against diseases caused by parasitic helminths and that, preferably, also protects animals from infection by such helminths.

SUMMARY OF THE INVENTION

The present invention relates to a novel product and process for prevention and treatment of parasitic helminth infection. According to the present invention there are provided parasitic helminth larval thiol specific antioxidant (TSA) proteins; parasitic helminth nucleic acid molecules, including those that encode such proteins; antibodies raised against such TSA proteins (anti-parasitic helminth TSA antibodies); and compounds that inhibit parasitic helminth larval TSA activity (i.e, inhibitory compounds or inhibitors).

The present invention also includes methods to obtain such proteins, nucleic acid molecules, antibodies and inhibitory compounds. Also included in the present invention are therapeutic compositions comprising such proteins, nucleic acid molecules, antibodies, and/or inhibitory compounds, as well as use of such therapeutic compositions to protect animals from diseases caused by parasitic helminths.

One embodiment of the present invention is an isolated nucleic acid molecule that hybridizes under stringent hybridization conditions with a *Dirofilaria immitis* (*D. immitis*) L4 (i.e., fourth stage larval) TSA gene, such nucleic acid molecules are referred to as parasitic helminth larval TSA nucleic acid molecules. A *D. immitis* L4 TSA gene preferably includes nucleic acid SEQ ID NO:1 and/or SEQ ID NO:3.

The present invention also relates to recombinant molecules, recombinant viruses and recombinant cells that include a TSA nucleic acid molecule of the present invention. Also included are methods to produce such nucleic acid molecules, recombinant molecules, recombinant viruses and recombinant cells.

Another embodiment of the present invention includes a parasitic helminth larval thiol specific antioxidant (TSA) protein (i.e., a parasitic helminth TSA protein) or a protein that includes a parasitic helminth larval TSA protein. A preferred parasitic helminth larval TSA protein comprises amino acid sequence SEQ ID NO:2.

The present invention also relates to mimetopes of parasitic helminth larval TSA proteins as well as to isolated antibodies that selectively bind to parasitic helminth larval TSA proteins or mimetopes thereof. Also included are methods, including recombinant methods, to produce proteins, mimetopes and antibodies of the present invention.

Another embodiment of the present invention is a method to identify a compound capable of inhibiting TSA activity, comprising the steps of: (a) contacting an isolated parasitic helminth L4 TSA protein with a putative inhibitory compound under conditions in which, in the absence of the compound, the protein has TSA activity; and (b) determining if the putative inhibitory compound inhibits the TSA activity. Also included in the present invention is a test kit to identify a compound capable of inhibiting TSA activity. Such a test kit includes an isolated parasitic helminth larval TSA protein having TSA activity and a means for determining the extent of inhibition of the TSA activity in the presence of a putative inhibitory compound.

Yet another embodiment of the present invention is a therapeutic composition that is capable of protecting an animal from disease caused by a parasitic helminth. Such a therapeutic composition includes one or more of the following protective compounds: an isolated parasitic helminth larval TSA protein or a mimetope thereof; an isolated nucleic acid molecule that hybridizes under stringent hybridization conditions with a *D. immitis* L4 TSA gene; an isolated antibody that selectively binds to a parasitic helminth larval TSA protein; and/or an inhibitor of TSA protein activity identified by its ability to inhibit parasitic helminth L4 TSA activity. A preferred therapeutic composition of the present invention also includes an excipient, an adjuvant and/or a carrier. Preferred TSA nucleic acid molecule compounds of the present invention include naked nucleic acid vaccines, recombinant virus vaccines and recombinant cell vaccines. Also included in the present invention is a method to protect an animal from disease caused by a parasitic helminth, comprising the step of administering to the animal a therapeutic composition of the present invention.

DETAILED DESCRIPTION OF THE INVENTION

The present invention provides for isolated parasitic helminth larval thiol specific antioxidant (TSA) proteins, isolated parasitic helminth larval TSA nucleic acid molecules, antibodies directed against parasitic helminth larval TSA proteins and other inhibitors of parasitic helminth larval TSA activity. As used herein, the terms isolated parasitic helminth larval TSA proteins and isolated parasitic helminth larval TSA nucleic acid molecules refers to TSA proteins and TSA nucleic acid molecules derived from parasitic helminth larvae and, as such, can be obtained from their natural source, can be produced using, for example, recombinant nucleic acid technology or chemical synthesis. Also included in the present invention is the use of these proteins, nucleic acid molecules, antibodies and other inhibitors as therapeutic compositions to protect animals from parasitic helminth diseases as well as in other applications, such as those disclosed below.

Parasitic helminth larval TSA proteins and nucleic acid molecules of the present invention have utility because they represent novel targets for anti-parasite vaccines and drugs. The products and processes of the present invention are advantageous because they enable the inhibition of parasite defense mechanisms that involve TSA. While not being bound by theory, it is believed that TSA proteins can defend parasitic helminths from damage of proteins, DNA or lipids by reactive oxygen radicals by inhibiting oxygen ($O_2$) radical-dependent inactivation of parasite cellular enzymes. The present invention is particularly advantageous because the proteins of the present invention were identified using sera isolated from dogs immune to Dirofilaria immitis infection, thereby suggesting the importance of the proteins as protective antigens.

One embodiment of the present invention is an isolated protein comprising a parasitic helminth larval TSA protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

As used herein, an isolated parasitic helminth larval TSA protein can be a full-length protein or any homolog of such a protein. An isolated protein of the present invention, including a homolog, can be identified in a straight-forward manner by the protein's ability to elicit an immune response against parasitic helminth larval TSA proteins, to reduce peroxide and/or to selectively bind to immune serum. Examples of TSA homologs include TSA proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a parasitic helminth larval TSA protein. That is, when the homologue is administered to an animal as an immunogen, using techniques known to those skilled in the art, the animal will produce an immune response against at least one epitope of a natural parasitic helminth larval TSA protein. The ability of a protein to effect an immune response, can be measured using techniques known to those skilled in the art. TSA protein homologs of the present invention also include TSA proteins that reduce peroxide and/or that selectively bind to immune serum. Examples of methods to measure such activities are disclosed herein, and are known to those skilled in the art. As used herein, the term "selectively binds to" immune serum refers to the ability of isolated proteins and mimetopes thereof to bind to serum collected from animals that are immune to parasitic helminth infection, in particular *D. immitis* infection, but essentially not to bind, according to standard detection techniques, to serum collected from animals that are not immune to parasitic helminth infection. Methods to produce and use immune serum are disclosed, for example, in Grieve et al., PCT Publication No. WO 94/15593, published Jul. 21, 1994, which is incorporated by reference herein in its entirety.

Parasitic helminth larval TSA protein homologs can be the result of natural allelic variation or natural mutation. TSA protein homologs of the present invention can also be produced using techniques known in the art including, but not limited to, direct modifications to the protein or modifications to the gene encoding the protein using, for example, classic or recombinant DNA techniques to effect random or targeted mutagenesis.

Isolated larval proteins of the present invention have the further characteristic of being encoded by nucleic acid molecules that hybridize under stringent hybridization conditions to a gene encoding a *D. immitis* L4 TSA protein (i.e., a *D. immitis* TSA gene). As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Such standard conditions are disclosed, for example, in Sambrook et al., 1989, *Molecular Cloning: A Laboratory Manual,* Cold Spring Harbor Labs Press. The reference Sambrook et al., ibid., is incorporated by reference herein in its entirety. Examples of such conditions include, but are not limited to, the following. Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 5×SSPE, 1% Sarkosyl, 5×Denhardts and 0.1 mg/ml denatured salmon sperm DNA at 37° C. for about 2 to 12 hours. The filters are then washed 3 times in a wash solution containing 5×SSPE, 1% Sarkosyl at 37° C. for about 15 minutes each. The filters can be further washed in a wash solution containing 2×SSPE, 1% Sarkosyl at 37° C. for about 15 minutes per wash. Randomly primed DNA probes can be hybridized, for example, to nucleic acid molecules typically immobilized on a filter (e.g., nitrocellulose filter) in a solution containing 5×SSPE, 1% Sarkosyl, 0.5% Blotto (dried milk in water), and 0.1 mg/ml denatured salmon sperm DNA at 42° C. for about 2 to about 12 hours. The filters are then washed 2 times in a wash solution containing 5×SSPE, 1% Sarkosyl at 42° C. for about 15 minutes each, followed by 2 washes in a wash solution containing 2×SSPE, 1% Sarkosyl at 42° C. for about 15 minutes each.

As used herein, a *D. immitis* L4 TSA gene includes all nucleic acid sequences related to a natural *D. immitis* L4 TSA gene such as regulatory regions that control production of the *D. immitis* L4 TSA protein encoded by that gene (such as, but not limited to, transcription, translation or post-translation control regions) as well as the coding region itself. In one embodiment, a *D. immitis* L4 TSA gene of the present invention includes the nucleic acid sequence SEQ ID NO:1, as well as the complement of SEQ ID NO:1. Nucleic acid sequence SEQ ID NO:1 represents the deduced sequence of the coding strand of the apparent coding region of a cDNA (complementary DNA) nucleic acid molecule denoted herein as $nDiTSA_{737}$, the production of which is disclosed in the Examples. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:1 (as well as other nucleic acid and protein sequences presented herein), at best, represents an apparent nucleic acid sequence of the nucleic acid molecule encoding a *D. immitis* TSA protein of the present invention.

In another embodiment, a *D. immitis* L4 TSA gene can be an allelic variant that includes a similar but not identical sequence to SEQ ID NO:1 and SEQ ID NO:3. An allelic variant of a *D. immitis* L4 TSA gene including SEQ ID NO:1 and SEQ ID NO:3, is a gene that occurs at essentially the same locus (or loci) in the genome as the gene including SEQ ID NO:1 and SEQ ID NO:3, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given parasitic helminth since the genome is diploid and/or among a group of two or more parasitic helminths.

The minimal size of a TSA protein homologue of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a TSA protein homologue of the present invention is from about 12 to about 18 nucleotides in length. Thus, the minimal size of a TSA protein homologue of the present invention is from about 4 to about 6 amino acids in length. There is no limit, other than a practical limit, on the maximal size of such a nucleic acid molecule in that the nucleic acid molecule can include a portion of a gene, an entire gene, or multiple genes, or portions thereof. The preferred size of a protein encoded by a nucleic acid molecule of the present invention depends on whether a full-length, fusion, multivalent, or functional portion of such a protein is desired.

One embodiment of the present invention includes a parasitic helminth larval TSA protein having TSA enzyme activity. Such a TSA protein preferably includes one or both cysteine (Cys) residues corresponding to the Cys at position 47 and the Cys residue at position 170 of the yeast TSA protein, assuming the initiating methionine is residue 1. One or both of these Cys residues in yeast TSA, and more specifically the VCP (valine-cysteine-proline) motifs, are believed to be involved in substrate peroxide reduction. Methods to detect peroxide reduction are described in the Examples section, as well as, for example, in Rhee et al., 1994, *Mol. Cells* 4: 137–142; Lim et al, 1993, *Biochem. Biophys. Res. Comm.* 192, 273–280; Sauri et al, 1995, *Biochem. Biophys. Res. Comm.* 208, 964–969; and Kim et al, 1988, *J. Biol. Chem.* 263, 4704–4711. These references are incorporated by reference herein in their entireties.

Suitable parasitic helminths from which to isolate TSA proteins of the present invention (including isolation of the natural protein or production of the protein by recombinant or synthetic techniques) include nematodes, cestodes, and trematodes, with nematodes being preferred. Preferred nematodes from which to isolate TSA proteins include filariid, ascarid, capillarid, strongylid, strongyloides, trichostrongyle, and trichurid nematodes. Particularly preferred nematodes are those of the genera Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Echinococcus, Enterobius, Filaroides, Haemonchus, Lagochilascaris, Loa, Mansonella, Muellerius, Nanophyetus, Necator, Nematodirus, Oesophagostomum, Onchocerca, opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Taenia, Thelazia, Toxascaris, Toxocara, Trichinella, Trichostrongylus, Trichuris, Uncinaria, and Wuchereria. Preferred filariid nematodes include Dirofilaria, Onchocerca, Acanthocheilonema, Brugia, Dipetalonema, Loa, Parafilaria, Setaria, Stephanofilaria and Wuchereria filariid nematodes, with *D. immitis* being even more preferred.

A preferred parasitic helminth larval TSA protein of the present invention is a compound that when administered to an animal in an effective manner, is capable of protecting that animal from disease caused by a parasitic helminth. In accordance with the present invention, the ability of a TSA protein of the present invention to protect an animal from disease by a parasitic helminth refers to the ability of that protein to, for example, treat, ameliorate and/or prevent disease caused by parasitic helminths. In one embodiment, a TSA protein of the present invention can elicit an immune response (including a humoral and/or cellular immune response) against a parasitic helminth.

Suitable parasites to target include any parasite that is essentially incapable of causing disease in an animal administered a TSA protein of the present invention. As such, a parasite to target includes any parasite that produces a protein having one or more epitopes that can be targeted by a humoral and/or cellular immune response against a TSA protein of the present invention and/or that can be targeted by a compound that otherwise inhibits TSA activity (e.g., a compound that inhibits peroxide reductase activity), thereby resulting in the decreased ability of the parasite to cause disease in an animal. Preferred parasites to target include parasitic helminths disclosed herein as being useful in the production of parasitic helminth proteins of the present invention.

The present invention also includes mimetopes of TSA proteins of the present invention. As used herein, a mimetope of a TSA protein of the present invention refers to any compound that is able to mimic the activity of such a TSA protein, often because the mimetope has a structure that mimics the TSA protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of a parasitic helminth larval TSA protein of the present invention is a fusion protein that includes a parasitic helminth larval TSA protein-containing domain attached to one or more fusion segments. Suitable fusion segments for use with the present invention include, but are not limited to, segments that can: enhance a protein's stability; act as an immunopotentiator to enhance an immune response against a TSA protein; and/or assist purification of a TSA protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the TSA-containing domain of the protein and can be susceptible to cleavage in order to enable straight-forward recovery of a TSA protein. Fusion proteins are preferably produced by culturing a recombinant cell transformed with a fusion nucleic acid molecule that encodes a protein including the fusion segment attached to either the carboxyl and/or amino terminal end of a TSA-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of particularly preferred fusion proteins of the present invention include PβGAL-PDiTSA$_{199}$ and PHIS-PDiTSA$_{199}$, production of which are disclosed herein.

In another embodiment, a parasitic helminth larval TSA protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a TSA protein of the present invention attached to one or more compounds protective against one or more other infectious agents, particularly an agent that infects humans, cats, dogs, cattle and/or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related microorganisms (e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In one embodiment, a parasitic helminth larval TSA protein of the present invention is attached to one or more additional compounds protective against heartworm. In another embodiment, one or more protective compounds, such as those listed above, can be included in a multivalent vaccine comprising a parasitic helminth larval TSA protein of the present invention and one or more other protective molecules as separate compounds.

A preferred isolated protein of the present invention is a protein encoded by a nucleic acid molecule that hybridizes under stringent hybridization conditions with nucleic acid molecules $nDiTSA_{737}$, and particularly with $nDiTSA_{600}$. A further preferred isolated protein is encoded by a nucleic acid molecule that hybridizes under stringent hybridization conditions with the complement of a nucleic acid molecule having nucleic acid sequence SEQ ID NO:1, and particularly SEQ ID NO:4. The complement of SEQ ID NO:1 is referred to herein as SEQ ID NO:3; the complement of SEQ ID NO:4 is referred to herein as SEQ ID NO:5.

Translation of SEQ ID NO:1 suggests that nucleic acid molecule $nDiTSA_{737}$ encodes a full-length parasitic helminth TSA protein of about 199 amino acids, referred to herein as $PDiTSA_{199}$, represented by SEQ ID NO:2, assuming an open reading frame having an initiation (start) codon spanning from about nucleotide 6 through about nucleotide 8 of SEQ ID NO:1 and a termination (stop) codon spanning from about nucleotide 603 through about nucleotide 605 of SEQ ID NO:1. The coding region encoding $PDiTSA_{199}$, and including the stop codon, is represented by nucleic acid molecule $nDiTSA_{600}$, having the nucleic acid sequence represented by SEQ ID NO:4 (the coding strand) and SEQ ID NO:5 (the complementary strand). The deduced amino acid sequence SEQ ID NO:2 suggests a protein having a molecular weight of about 22.1 kilodaltons (kD) and an estimated pI of about 6.61.

Comparison of amino acid sequence SEQ ID NO:2 (i.e., the amino acid sequence of $PDiTSA_{199}$) with amino acid sequences reported in GenBank indicates that SEQ ID NO:2, showed some homology to TSA proteins of eukaryotic origin. The highest scoring match, i.e., about 75% identity, was found between SEQ ID NO:2 and C. elegans putative TSA protein (Genbank Accession No. U37429).

More preferred parasitic helminth larval TSA proteins of the present invention include proteins comprising amino acid sequences that are at least about 80%, preferably at least about 85%, and more preferably at least about 90%, and even more preferably at least about 95% identical to amino acid sequence SEQ ID NO:2.

More preferred parasitic helminth larval TSA proteins of the present invention include proteins encoded by a nucleic acid molecule comprising at least a portion of $nDiTSA_{737}$, of $nDiTSA_{600}$, or of allelic variants of such nucleic acid molecules. More preferred is a TSA protein encoded by $nDiTSA_{600}$ or by an allelic variant of $nDiTSA_{600}$. Particularly preferred is $PDiTSA_{199}$. In one embodiment, a preferred TSA protein of the present invention is encoded by at least a portion of SEQ ID NO:1 or SEQ ID NO:4 and, as such, has an amino acid sequence that includes at least a portion of SEQ ID NO:2. Also preferred is a protein encoded by an allelic variant of a nucleic acid molecule comprising at least a portion of SEQ ID NO:1 or SEQ ID NO:4. Particularly preferred TSA proteins of the present invention include SEQ ID NO:2 (including, but not limited to, the proteins consisting of SEQ ID NO:2, fusion proteins and multivalent proteins) and proteins encoded by allelic variants of SEQ ID NO:4.

Another embodiment of the present invention is an isolated nucleic acid molecule that hybridizes under stringent hybridization conditions with a D. immitis L4 TSA gene. The identifying characteristics of such a gene is heretofore described. A nucleic acid molecule of the present invention can include an isolated natural parasitic helminth larval TSA gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with a D. immitis L4 TSA gene under stringent hybridization conditions. Suitable and preferred parasitic helminths are disclosed above.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated parasitic helminth larval TSA nucleic acid molecule of the present invention can be isolated from its natural source or produced using recombinant DNA technology (e.g., polymerase chain reaction (PCR) amplification, cloning) or chemical synthesis. Isolated TSA nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode a TSA protein of the present invention or to form stable hybrids under stringent conditions with natural gene isolates.

A parasitic helminth larval TSA nucleic acid molecule homologue can be produced using a number of methods known to those skilled in the art (see, for example, Sambrook et al., ibid.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Nucleic acid molecule homologs can be selected by hybridization with a D. immitis L4 TSA gene or by screening the function of a protein encoded by the nucleic acid molecule (e.g., ability to elicit an immune response against at least one epitope of a parasitic helminth larval TSA protein, ability to selectively bind to immune serum, peroxide reductase activity).

An isolated nucleic acid molecule of the present invention can include a nucleic acid sequence that encodes at least one parasitic helminth larval TSA protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth larval TSA protein.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., a TSA protein of the present invention), the nucleic acid molecule being delivered to the animal, for example, by direct injection (i.e, as a naked nucleic acid) or in a vehicle such as a recombinant virus vaccine or a recombinant cell vaccine.

One embodiment of the present invention is a parasitic helminth larval TSA nucleic acid molecule that hybridizes under stringent hybridization conditions with nucleic acid molecule $nDiTSA_{737}$ and preferably with a nucleic acid molecule having nucleic acid sequence SEQ ID NO:1 or SEQ ID NO:3.

Comparison of nucleic acid sequence SEQ ID NO:1 (i.e., the nucleic acid sequence of $nDiTSA_{737}$) with nucleic acid sequences reported in GenBank indicates that SEQ ID NO:1, showed some homology to TSA genes of eukaryotic origin. The highest scoring match, i.e., about 70% identity, was found between SEQ ID NO:4 and a *C. elegans* gene that encodes a putative TSA protein.

Preferred parasitic helminth larval TSA nucleic acid molecules include nucleic acid molecules having a nucleic acid sequence that is at least about 75%, preferably at least about 80%, more preferably at least about 85%, even more preferably at least about 90% and even more preferably at least about 95% identical to nucleic acid sequence SEQ ID NO:4 or SEQ ID NO:5.

Another embodiment of the present invention is any parasitic helminth, including adult, TSA nucleic acid molecule that hybridizes under stringent hybridization conditions to a gene encoding a *D. immitis* L4 TSA protein. Also included are parasitic helminth adult TSA proteins encoded by such nucleic acid molecules, as well as uses of such nucleic acid molecules and proteins, such as those disclosed herein. Particularly preferred are *D. immitis* adult TSA nucleic acid molecules, such as those identified in the Examples section, and *D. immitis* adult TSA proteins encoded by such nucleic acid molecules.

Another preferred nucleic acid molecule of the present invention includes at least a portion of nucleic acid sequence SEQ ID NO:1 and/or SEQ ID NO:3, that is capable of hybridizing to a *D. immitis* L4 TSA gene of the present invention, and allelic variants of SEQ ID NO:1 and/or SEQ ID NO:3. A more preferred nucleic acid molecule includes the nucleic acid sequence SEQ ID NO:1, SEQ ID NO:3, SEQ ID NO:4, and/or SEQ ID NO:5, as well as allelic variants thereof. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include $nDiTSA_{737}$ and $nDiTSA_{600}$.

The present invention also includes a nucleic acid molecule encoding a protein having at least a portion of SEQ ID NO:2, including nucleic acid molecules that have been modified to accommodate codon usage properties of the cells in which such nucleic acid molecules are to be expressed.

Knowing the nucleic acid sequences of certain parasitic helminth TSA nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain TSA nucleic acid molecules from other parasitic helminths. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include parasitic helminth L3, L4 or adult cDNA libraries as well as genomic DNA libraries. Similarly, preferred DNA sources to screen or from which to amplify nucleic acid molecules include parasitic helminth L3, L4 or adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising parasitic helminth larval TSA genes or other parasitic helminth larval TSA nucleic acid molecules. oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit TSA protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention also includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of parasitic helminth larval TSA nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7ac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic helminths, such as, *D. immitis*.

Suitable and preferred nucleic acid molecules to include in recombinant vectors of the present invention are as disclosed herein. Preferred nucleic acid molecules to include in recombinant vectors, and particularly in recombinant molecules, include $nDiTSA_{737}$ and $nDiTSA_{600}$. Particularly preferred recombinant molecules of the present invention include pβgal-$nDiTSA_{737}$ and pHis-$nDiTSA_{600}$, the production of which are described in the Examples section.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include parasitic helminth larval TSA nucleic acid molecules disclosed herein. Particularly preferred nucleic acid molecules with which to transform a cell include $nDiTSA_{737}$ and $nDiTSA_{600}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing parasitic helminth larval TSA proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 $_\chi$3987 and SR-11 $_\chi$4072; *Spodoptera frugiperda*; *Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include pβgal-nDiTSA$_{737}$ and pHis-nDiTSA$_{600}$.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include *E. coli*:pβgal-nDiTSA$_{737}$ and *E. coli*:pHis-nDiTSA$_{600}$. Details regarding the production of these recombinant cells are disclosed herein.

Recombinant cells of the present invention can also be co-transformed with one or more recombinant molecules including parasitic helminth larval TSA nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated TSA proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a parasitic helminth TSA protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a parasitic helminth larval TSA protein of the present invention or a mimetope thereof (e.g., anti-parasitic helminth TSA antibodies). As used herein, the term "selectively binds to" a TSA protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-parasitic helminth TSA antibody preferably selectively binds to a parasitic helminth larval TSA protein in such a way as to reduce the activity of that protein.

Isolated antibodies of the present invention can include antibodies in serum, or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce parasitic helminth larval TSA proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. Therapeutic compositions of the present invention include at least one of the following protective compounds: an isolated parasitic helminth larval TSA protein or a mimetope thereof, an isolated nucleic acid molecule that hybridizes under stringent hybridization conditions with a D. immitis L4 TSA gene, an isolated antibody that selectively binds to a parasitic helminth larval TSA protein, an inhibitor of TSA protein activity identified by its ability to inhibit parasitic helminth larval TSA activity, and a mixture thereof (i.e., combination of at least two of the compounds). As used herein, a protective compound refers to a compound that, when administered to an animal in an effective manner, is able to treat, ameliorate, and/or prevent disease caused by a parasitic helminth of the present invention. Preferred helminths to target are heretofore disclosed. Examples of proteins, nucleic acid molecules, antibodies and inhibitors of the present invention are disclosed herein.

The present invention also includes a therapeutic composition comprising at least one parasitic helminth larval TSA-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm include dogs, cats, humans and ferrets, with dogs and cats being particularly preferred.

In one embodiment, a therapeutic composition of the present invention can be administered to the vector in which the parasitic helminth develops, such as to a mosquito in order to prevent the spread of heartworm. Such administration could be orally or by developing transgenic vectors capable of producing at least one therapeutic composition of the present invention. In another embodiment, a vector, such as a mosquito, can ingest therapeutic compositions present in the blood of a host that has been administered a therapeutic composition of the present invention.

In order to protect an animal from disease caused by a parasitic helminth of the present invention, a therapeutic composition of the present invention is administered to the animal in an effective manner such that the composition is capable of protecting that animal from a disease caused by a parasitic helminth. Therapeutic compositions of the present invention can be administered to animals prior to infection in order to prevent infection (i.e., as a preventative vaccine) and/or can be administered to animals after infection in order to treat disease caused by the parasitic helminth (i.e., as a therapeutic vaccine).

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and NIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents. Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a dicistronic recombinant molecule. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki Forest virus), species-specific herpesviruses and species-specific poxviruses being particularly preferred. Any suitable transcription control sequence can be used, including those disclosed as suitable for protein production. Particularly preferred transcription control sequence include cytomegalovirus immediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccines ranges from about 1 nanogram (ng) to about 100 µg, depending on the route of administration and/or method of delivery, as can be determined by those skilled in the art. Suitable delivery methods include, for example, by injection, as drops, aerosolized and/or topically. Naked DNA of the present invention can be contained in an aqueous excipient (e.g., phosphate buffered saline) alone or a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminth as disclosed herein. For example, a recombinant virus vaccine comprising a parasitic helminth TSA nucleic acid molecule of the present invention is administered according to a protocol that results in the animal producing a sufficient immune response to protect itself from heartworm. A preferred single dose of a recombinant virus vaccine of the present invention is from about $1\times10^4$ to about $1\times10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Challenge studies can include implantation of chambers including parasitic helminth larvae into the treated animal and/or direct administration of larvae to the treated animal. In one embodiment, therapeutic compositions can be tested in animal models such as mice. Such techniques are known to those skilled in the art.

One preferred embodiment of the present invention is the use of parasitic helminth larval TSA proteins, nucleic acid molecules, antibodies and inhibitory compounds of the present invention, to protect an animal from heartworm. It is particularly preferred to prevent L3 that are delivered to the animal by the mosquito intermediate host from maturing into adult worms. As such, preferred therapeutic compositions are those that are able to inhibit at least one step in the portion of the parasite's development cycle that includes L3, third molt, L4, fourth molt, immature adult prior to entering the circulatory system. In dogs, this portion of the development cycle is about 70 days. Particularly preferred therapeutic compositions include *D. immitis* larval TSA-based therapeutic compositions of the present invention, particularly since TSA is expressed in L3 and L4. Such compositions include *D. immitis* larval TSA nucleic acid molecules, *D. immitis* larval TSA proteins and mimetopes thereof, anti-*D. immitis* larval TSA antibodies, and inhibitors of *D. immitis* larval TSA activity. Therapeutic compositions are administered to animals in a manner effective to protect the animals from heartworm. Additional protection may be obtained by administering additional protective compounds, including other parasitic helminth proteins, nucleic acid molecules, antibodies and inhibitory compounds, as disclosed herein.

One therapeutic composition of the present invention includes an inhibitor of parasitic helminth TSA activity, i.e., a compound capable of substantially interfering with the function of a parasitic helminth TSA susceptible to inhibition by an inhibitor of parasitic helminth larval TSA activity. For example, an isolated protein or mimetope thereof, is administered in an amount and manner that elicits (i.e., stimulates) an immune response that is sufficient to protect the animal from the disease. similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of parasitic helminth larval TSA proteins in order to interfere with development of parasitic helminths targeted in accordance with the present invention.

An inhibitor of TSA activity can be identified using parasitic helminth larval TSA proteins of the present invention. One embodiment of the present invention is a method to identify a compound capable of inhibiting TSA activity of a parasitic helminth. Such a method includes the steps of (a) contacting (e.g., combining, mixing) an isolated parasitic helminth larval TSA protein, preferably a *D. immitis* larval TSA protein, with a putative inhibitory compound under conditions in which, in the absence of the compound, the protein has TSA activity, and (b) determining if the putative inhibitory compound inhibits the TSA activity. Putative inhibitory compounds to screen include small organic molecules, antibodies (including mimetopes thereof) and substrate analogs. Methods to determine TSA activity are known to those skilled in the art; see, for example, citations in background section and references included therein.

The present invention also includes a test kit to identify a compound capable of inhibiting TSA activity of a parasitic helminth. Such a test kit includes an isolated parasitic helminth larval TSA protein, preferably a *D. immitis* larval TSA protein, having TSA activity and a means for determining the extent of inhibition of TSA activity in the presence of (i.e., effected by) a putative inhibitory compound. Such compounds are also screened to identify those that are substantially not toxic in host animals.

TSA inhibitors isolated by such a method, and/or test kit, can be used to inhibit any TSA that is susceptible to such an inhibitor. Preferred TSA enzymes to inhibit are those produced by parasitic helminths. A particularly preferred TSA inhibitor of the present invention is capable of protecting an animal from heartworm. It is also within the scope of the present invention to use inhibitors of the present invention to target TSA-related disorders in animals. Therapeutic compositions comprising TSA inhibitory compounds of the present invention can be administered to animals in an effective manner to protect animals from disease caused by the targeted TSA enzymes, and preferably to protect animals from heartworm. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect other phases of the parasite's life cycle. Methods to use such diagnostic reagents to diagnose parasitic helminth infection are well known to those skilled in the art. Suitable and preferred parasitic helminths to detect are those to which therapeutic compositions of the present invention are targeted. A particularly preferred parasitic helminth to detect using diagnostic reagents of the present invention is Dirofilaria.

The following examples are provided for the purposes of illustration and are not intended to limit the scope of the present invention.

EXAMPLES

Example 1

This Example describes the isolation and sequencing of several *D. immitis* TSA nucleic acid molecules of the present invention. It is to be noted that the Examples include a number of molecular biology, microbiology, immunology and biochemistry techniques considered to be known to those skilled in the art. Disclosure of such techniques can be found, for example, in Sambrook et al., ibid. and related references.

A *D. immitis* TSA nucleic acid molecule of about 737 nucleotides, denoted nDiTSA$_{737}$, was identified by its ability to encode a protein that selectively bound to at least one component of immune serum collected from a dog immunized with *D. immitis* larvae. Immune serum was produced and used as described in WO 94/15593, ibid. Specifically, a *D. immitis* L4 cDNA expression library was constructed in Uni-ZAP™ XR vector (available from Stratagene Cloning Systems, La Jolla, Calif.), using Stratagene's ZAP-cDNA Synthesis Kit protocol and L4 mRNAs. Using the protocol described in the Stratagene picoBlue immunoscreening kit, the L4 cDNA expression library was screened with immune dog sera, prepared as described in WO 94/15593, ibid. Immunoscreening of duplicate plaque lifts of the cDNA library with the same immune dog serum identified a clone containing nucleic acid molecule nDiTSA$_{737}$.

The plaque-purified clone including *D. immitis* nucleic acid sequence nDiTSA$_{737}$ was converted into a double stranded recombinant molecule, herein denoted as pβgal-nDiTSA$_{737}$, using ExAssist™ helper phage and SOLR™ *E. coli* according to the in vivo excision protocol described in the Stratagene ZAP-cDNA Synthesis Kit. Double stranded plasmid DNA was prepared using an alkaline lysis protocol, such as that described in Sambrook et al., ibid. The plasmid DNA was digested with EcoRI and XhoI restriction endonucleases to release a single *D. immitis* nDiTSA$_{737}$ DNA fragment of about 737 nucleotides in size.

The plasmid containing *D. immitis* nDiTSA$_{737}$ was sequenced using the Sanger dideoxy chain termination method, as described in Sambrook et al., ibid. An about 737 nucleotide consensus sequence of the entire *D. immitis* nDiTSA$_{737}$ DNA fragment was determined; the sequences of the two complementary strands are presented as SEQ ID NO:1 and SEQ ID NO:3. The *D. immitis* nDiTSA$_{737}$ sequence represents a full length cDNA clone. The apparent start and stop codons span nucleotides from about 6 through 8 and from about 603 through 605, respectively, of SEQ ID NO:1.

Translation of SEQ ID NO:1 yields a protein of about 199 amino acids, denoted PDiTSA$_{199}$, the amino acid sequence of which is presented in SEQ ID NO:2. The coding region of PDiTSA$_{199}$ is referred to herein as nDiTSA$_{600}$, the nucleic acid sequence of which is represented in SEQ ID NO:4 (the coding strand) and SEQ ID NO:5 (the complementary strand). The amino acid sequence of *D. immitis* PDiTSA$_{199}$ (i.e., SEQ ID NO:2) predicts that PDiTSA$_{199}$ has an estimated molecular weight of about 22.1 kD and an estimated pI of about 6.61.

To confirm the *D. immitis* origin of the isolated TSA cDNA nucleic acid molecules, a Southern blot containing about 10 micrograms of EcoRI restricted *D. immitis* genomic DNA, canine genomic DNA and *Aedes aegypti* genomic DNA was hybridized under stringent conditions with pβgal-nDiTSA$_{737}$ DNA radiolabeled by random priming with the Megaprime DNA Labeling System (available from Amersham Life Science, Arlington Heights, Ill.). The probe detected a single high molecular weight band only in the *D. immitis* genomic DNA.

A homology search of the non-redundant protein sequence database was performed through the National Center for Biotechnology Information using the BLAST network. This database includes +SwissProt+PIR+SPUpdate+GenPept+GPUpdate. The search was performed using SEQ ID NO:2 and showed significant homology to thiol-specific antioxidant proteins of prokaryotic and eukaryotic origins, spanning from about amino acid 1 through about amino acid 199 of SEQ ID NO:2. The highest scoring match of the homology search at the amino acid level was Genbank accession number U37429: *Caenorhabditis elegans* cosmid F09E5, about 75.5% identical. At the nucleotide level, the coding regions represented in SEQ ID NO:4 were most similar to that of the putative TSA coding region within the *C. elegans* cosmid joining exon regions 38986–39361 and 39426–39637, being about 70% identical.

Example 2

This Example discloses the production of a recombinant cell of the present invention.

Recombinant molecule pHis-nDiTSA$_{600}$, containing *D. immitis* TSA nucleotides from about 6 through about 605 operatively linked to trc transcription control sequences and to a fusion sequence encoding a poly-histidine segment comprising 6 histidines was produced in the following manner. An about 600-nucleotide DNA fragment containing nucleotides spanning from about 6 through about 605 of SEQ ID NO:1, denoted herein as nDiTSA$_{600}$, was PCR amplified from nucleic acid molecule D. immitis nDiTSA$_{737}$, produced as described in Example 1, using the primers TSABam HI sense primer 5' GGATCCCAT-GACTCTTGCTGG 3' (denoted herein as SEQ ID NO:6; BamHI site in bold) and TSAEcoRI antisense 5' GAATTCT-CAGTGCTTTTCGAAGTACGC 3' (denoted herein as SEQ ID NO:7; EcoRI site in bold). Recombinant molecule pHis-nDiTSA$_{600}$ was produced by digesting the nDiTSA$_{600}$-containing PCR product with BamHI and EcoRI restriction endonucleases, gel purifying the resulting fragment and directionally subcloning it into expression vector pTrcHisB (available from Invitrogen, San Diego, Calif.) that had been cleaved with BamHI and EcoRI and gel purified.

Recombinant molecule pHis-nDiTSA$_{600}$ was transformed into E. coli to form recombinant cell E. coli:pHis-nDiTSA$_{600}$ using standard techniques as disclosed in Sambrook et al., ibid.

Example 3

This Example discloses the production of a TSA protein of the present invention in a prokaryotic cell as well as studies to characterize that protein.

Recombinant cell E. coli:pHis-nDiTSA$_{600}$, produced as described in Example 2, was cultured in shake flasks containing an enriched bacterial growth medium containing 0.1 mg/ml ampicillin at about 37° C. When the cells reached an OD$_{600}$ of about 0.5, expression of D. immitis nDiTSA$_{600}$ was induced by addition of about 0.5 mM isopropyl-β-D-thiogalactoside (IPTG), and the cells were cultured for about 1.5 hours at about 37° C. Protein production was monitored by SDS PAGE of recombinant cell lysates, followed by Coomassie blue staining, using standard techniques. Recombinant cell E. coli:pHis-nDiTSA$_{600}$ produced a fusion protein, denoted herein as PHIS-PDiTSA$_{199}$, that migrated with an apparent molecular weight of about 26 kD.

Immunoblot analysis of recombinant cell E. coli:pHis-nDiTSA$_{600}$ lysates indicated that the about 26 kD protein was able to bind to a T7 tag monoclonal antibody (available from Novagen, Inc., Madison, Wis.) directed against the fusion portion of the recombinant PHIS-PDiTSA$_{199}$ fusion protein.

The PHIS-PDiTSA$_{199}$ histidine fusion protein was separated from E. coli proteins by nickel chelation chromatography with a pH gradient elution. Immunoblot analysis of the E. coli:pHis-nDiTSA$_{600}$ lysate, column eluate and column void volume indicated that the PHIS-PDiTSA$_{199}$ 26 kD protein isolated using nickel column chromatography was able to selectively bind to a T7 tag monoclonal antibody.

Example 4

This Example discloses the purification of a TSA fusion protein of the present invention from total cell lysates.

TSA fusion protein PHIS-PDiTSA$_{199}$, produced as described in Example 3, was separated from E. coli proteins by continuous-elution electrophoresis through a 14% acrylamide-SDS cylindrical gel (BioRad PrepCell™, available from BioRad Laboratories, Hercules, Calif.). As the proteins migrated off the bottom of the gel, the individual bands of protein were collected in 1.5 ml fractions. Immunoblot analysis of the resulting fractions indicated that fractions 48, 49, 50 and 51 contained the PHIS-PDiTSA$_{199}$ 26 kD protein in that those fractions included a protein capable of selectively binding to a T7 tag monoclonal antibody, such as that described in Example 3. Colloidal gold staining of Western blots containing the 4 fractions indicated that the 26 kD protein was significantly purified from other E. coli proteins. Fractions 48, 50 and 51 were pooled and dialyzed against 1× PBS to produce PrepCell-purified PHIS-PDiTSA$_{199}$. Fractions 40–44, which did not selectively bind to the T7 tag monoclonal antibody, were pooled and dialyzed against 1× PBS to produce PrepCell-purified Control.

The fourth fraction containing PHIS-PDiTSA$_{199}$ was used to immunize a rabbit following an immunization strategy of three administrations of the TSA protein.

Example 5

This Example describes the isolation and sequencing of several D. immitis nucleic acid molecules of the present invention.

D. immitis TSA nucleic acid molecules were PCR amplified from D. immitis life stage specific cDNA expression libraries constructed from L3, L4, adult male and adult female mRNAs as described in Example 1. D. immitis TSA PCR products of about 650 to about 730 nucleotides were amplified from these templates using the following primers: a sense primer spanning nucleotides from about 141 through about 176 of SEQ ID NO:1 and having the nucleic acid sequence 5' CCTCTCGATTTCACTTTCGTTTGCCCAA-CAGAGATA 3' (denoted herein as SEQ ID NO:8); and T7X, a vector antisense primer having nucleic acid sequence 5' GTAATACGACTCACTATAGGGC 3' (denoted herein as SEQ ID NO:9). The nucleic acid sequence in SEQ ID NO:8 encodes a three amino acid motif which is conserved in all TSA molecules currently in the databases, specifically: NH$_2$-PLDFTFVCPTEI—COOH (conserved amino acid motif in bold).

To confirm that the resulting PCR products were TSA specific, a Southern blot containing about 0.25 μg of PCR product was hybridized under stringent conditions with a D. immitis TSA specific antisense probe spanning nucleotides 451 through 471 of SEQ ID NO:1 and having nucleic acid sequence 5' CATCTACAGAACGACCAACTG 3' (SEQ ID NO:10). The probe DNA was radiolabeled at the 5' end using T4 polynucleotide kinase (available from Promega Corp., Madison, Wis.). The probe detected two bands of about 650 and 720 nucleotides in the L3 cDNA sample (denoted herein as nDiTSA(L3)$_{650}$ and nDiTSA(L3)$_{720}$), in the adult male cDNA sample (denoted herein as nDiTSA(Adm)$_{650}$ and nDiTSA(Adm)$_{720}$), and in the adult female cDNA sample (denoted herein as nDiTSA(Adf)$_{650}$ and nDiTSA(Adf)$_{720}$). The probe detected one band of about 650 nucleotides in the L4 cDNA sample (denoted herein as nDiTSA(L4)$_{650}$.

Nucleic acid molecules nDiTSA(L3)$_{650}$, nDiTSA(L3)$_{720}$, nDiTSA(Adm)$_{720}$, nDiTSA(Adf)$_{720}$, and nDiTSA(L4)$_{650}$ were gel isolated, cloned into the TA cloning vector (available from Invitrogen, San Diego, Calif.) and submitted for automated sequence analysis.

Example 6

This Example demonstrates the enzyme activity of the recombinant PHIS-PDiTSA$_{199}$ fusion protein based on an assay in which DNA cleavage by mixed function oxidase (MFO) systems can be inactivated by active forms of TSA.

In an assay similar to that described, for example, by Lim et al, ibid., 273–280; and Sauri et al, ibid., supercoiled pBS plasmid (available from Stratagene) was exposed to an MFO system consisting of oxidative reactions involving thiol/Fe$^{+3}$/O$_2^-$, in the presence of either PrepCell-purified PHIS-PDiTSA$_{199}$ or PrepCell-purified Control, produced as described in Example 4. At least a portion of the double stranded supercoiled plasmid (form I) was converted to a relaxed double stranded circle (form II) in the presence of PrepCell-purified Control. Such nicking activity was suppressed in the presence of about 50–100 μg per milliliter (ml) PrepCell-purified PHIS-PDiTSA$_{199}$. This assay indicates that PHIS-PDiTSA$_{199}$ is an active TSA protein and, as such, that nucleic acid molecule nDiTSA$_{600}$ encodes a TSA protein having thiol antioxidant activity.

---

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 737 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 6..605

(xi) SEQUENCE DESCRIPTION: SEQ ID NO:1:

```
AAGAA ATG ACT CTT GCT GGA AGC AAA GCA TTC ATT GGT CAA CCG GCC        47
      Met Thr Leu Ala Gly Ser Lys Ala Phe Ile Gly Gln Pro Ala
       1               5                  10

CCT AAT TTC AAA ACA ACA GCG GTT GTG AAT GGC GAT TTC AAG GAA ATT      95
Pro Asn Phe Lys Thr Thr Ala Val Val Asn Gly Asp Phe Lys Glu Ile
 15              20                  25                  30

TCA CTT TGT CAG TTC AAA GGA AAA TAT GTG GTC CTC TTC TTT TAT CCT     143
Ser Leu Cys Gln Phe Lys Gly Lys Tyr Val Val Leu Phe Phe Tyr Pro
                 35                  40                  45

CTC GAT TTC ACT TTC GTT TGC CCA ACA GAG ATA ATT GCT TTT TCT GAT     191
Leu Asp Phe Thr Phe Val Cys Pro Thr Glu Ile Ile Ala Phe Ser Asp
             50                  55                  60

CGT ATT GCG GAG TTC AAA AAA TTA GAT GTA GCT GTT ATG GCA TGC TCA     239
Arg Ile Ala Glu Phe Lys Lys Leu Asp Val Ala Val Met Ala Cys Ser
         65                  70                  75

ACT GAT TCA CAT TTT TCA CAC CTT GCA TGG GTA AAT ACC GAC CGA AAA     287
Thr Asp Ser His Phe Ser His Leu Ala Trp Val Asn Thr Asp Arg Lys
     80                  85                  90

ATG GGT GGA CTC GGT CAG ATG AAT ATA CCA ATT CTT GCT GAT ACC AAT     335
Met Gly Gly Leu Gly Gln Met Asn Ile Pro Ile Leu Ala Asp Thr Asn
 95                 100                 105                 110

CAT ACA ATT AGT AGG GCA TAT GGC GTG CTC AAG GAA GAT GAT GGC ATT     383
His Thr Ile Ser Arg Ala Tyr Gly Val Leu Lys Glu Asp Asp Gly Ile
                115                 120                 125

GCT TAC CGT GGA TTA TTC ATC ATT GAT CCA AAA GGG ATT TTG CGA CAA     431
Ala Tyr Arg Gly Leu Phe Ile Ile Asp Pro Lys Gly Ile Leu Arg Gln
            130                 135                 140

ATC ACA ATC AAT GAT CTT CCA GTT GGT CGT TCT GTA GAT GAA ACT TTA     479
Ile Thr Ile Asn Asp Leu Pro Val Gly Arg Ser Val Asp Glu Thr Leu
        145                 150                 155

CGT CTG ATT CAA GCT TTT CAA TTT GTC GAC AAT CAC GGT GAA GTA TGT     527
Arg Leu Ile Gln Ala Phe Gln Phe Val Asp Asn His Gly Glu Val Cys
    160                 165                 170

CCG GCC AAT TGG CAG CCA GGA TCT GAA GCA ATC AAA CCT GGA GTG AAA     575
Pro Ala Asn Trp Gln Pro Gly Ser Glu Ala Ile Lys Pro Gly Val Lys
175                 180                 185                 190

GAA AGC AAA GCG TAC TTC GAA AAG CAC TGAAAACGTT GTACATTTCA           622
Glu Ser Lys Ala Tyr Phe Glu Lys His
```

-continued

```
                    195                 200
ACTATTTTGT GATTCTTTGA ATGAATGCTT GTTGATTGCA TTGGTGAAGA TGACATATCT      682

TTCTTTATTA TAAGTAATTG GTAAACACAT TGATTTTCAA AAAAAAAAAA AAAAA           737
```

(2) INFORMATION FOR SEQ ID NO:2:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Leu Ala Gly Ser Lys Ala Phe Ile Gly Gln Pro Ala Pro Asn
 1               5                  10                  15

Phe Lys Thr Thr Ala Val Val Asn Gly Asp Phe Lys Glu Ile Ser Leu
                20                  25                  30

Cys Gln Phe Lys Gly Lys Tyr Val Val Leu Phe Phe Tyr Pro Leu Asp
            35                  40                  45

Phe Thr Phe Val Cys Pro Thr Glu Ile Ile Ala Phe Ser Asp Arg Ile
    50                  55                  60

Ala Glu Phe Lys Lys Leu Asp Val Ala Val Met Ala Cys Ser Thr Asp
65                  70                  75                  80

Ser His Phe Ser His Leu Ala Trp Val Asn Thr Asp Arg Lys Met Gly
                85                  90                  95

Gly Leu Gly Gln Met Asn Ile Pro Ile Leu Ala Asp Thr Asn His Thr
            100                 105                 110

Ile Ser Arg Ala Tyr Gly Val Leu Lys Glu Asp Asp Gly Ile Ala Tyr
        115                 120                 125

Arg Gly Leu Phe Ile Ile Asp Pro Lys Gly Ile Leu Arg Gln Ile Thr
    130                 135                 140

Ile Asn Asp Leu Pro Val Gly Arg Ser Val Asp Glu Thr Leu Arg Leu
145                 150                 155                 160

Ile Gln Ala Phe Gln Phe Val Asp Asn His Gly Glu Val Cys Pro Ala
                165                 170                 175

Asn Trp Gln Pro Gly Ser Glu Ala Ile Lys Pro Gly Val Lys Glu Ser
            180                 185                 190

Lys Ala Tyr Phe Glu Lys His
        195
```

(2) INFORMATION FOR SEQ ID NO:3:

(i) SEQUENCE CHARACTERISTICS:
        (A) LENGTH: 737 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
TTTTTTTTTT TTTTTTTGAA ATCAATGTG TTTACCAATT ACTTATAATA AAGAAAGATA       60

TGTCATCTTC ACCAATGCAA TCAACAAGCA TTCATTCAAA GAATCACAAA ATAGTTGAAA     120

TGTACAACGT TTTCAGTGCT TTTCGAAGTA CGCTTTGCTT TCTTTCACTC CAGGTTTGAT     180

TGCTTCAGAT CCTGGCTGCC AATTGGCCGG ACATACTTCA CCGTGATTGT CGACAAATTG     240

AAAAGCTTGA ATCAGACGTA AAGTTTCATC TACAGAACGA CCAACTGGAA GATCATTGAT     300
```

```
TGTGATTTGT CGCAAAATCC CTTTTGGATC AATGATGAAT AATCCACGGT AAGCAATGCC      360

ATCATCTTCC TTGAGCACGC CATATGCCCT ACTAATTGTA TGATTGGTAT CAGCAAGAAT      420

TGGTATATTC ATCTGACCGA GTCCACCCAT TTTTCGGTCG GTATTTACCC ATGCAAGGTG      480

TGAAAAATGT GAATCAGTTG AGCATGCCAT AACAGCTACA TCTAATTTTT TGAACTCCGC      540

AATACGATCA GAAAAAGCAA TTATCTCTGT TGGGCAAACG AAAGTGAAAT CGAGAGGATA      600

AAAGAAGAGG ACCACATATT TTCCTTTGAA CTGACAAAGT GAAATTTCCT TGAAATCGCC      660

ATTCACAACC GCTGTTGTTT TGAAATTAGG GGCCGGTTGA CCAATGAATG CTTTGCTTCC      720

AGCAAGAGTC ATTTCTT                                                    737

(2) INFORMATION FOR SEQ ID NO:4:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ATGACTCTTG CTGGAAGCAA AGCATTCATT GGTCAACCGG CCCCTAATTT CAAAACAACA       60

GCGGTTGTGA ATGGCGATTT CAAGGAAATT TCACTTTGTC AGTTCAAAGG AAAATATGTG      120

GTCCTCTTCT TTTATCCTCT CGATTTCACT TTCGTTTGCC AACAGAGAT AATTGCTTTT      180

TCTGATCGTA TTGCGGAGTT CAAAAAATTA GATGTAGCTG TTATGGCATG CTCAACTGAT      240

TCACATTTTT CACACCTTGC ATGGGTAAAT ACCGACCGAA AAATGGGTGG ACTCGGTCAG      300

ATGAATATAC CAATTCTTGC TGATACCAAT CATACAATTA GTAGGGCATA TGGCGTGCTC      360

AAGGAAGATG ATGGCATTGC TTACCGTGGA TTATTCATCA TTGATCCAAA AGGGATTTTG      420

CGACAAATCA CAATCAATGA TCTTCCAGTT GGTCGTTCTG TAGATGAAAC TTTACGTCTG      480

ATTCAAGCTT TCAATTTGT CGACAATCAC GGTGAAGTAT GTCCGGCCAA TTGGCAGCCA      540

GGATCTGAAG CAATCAAACC TGGAGTGAAA GAAAGCAAAG CGTACTTCGA AAAGCACTGA      600

(2) INFORMATION FOR SEQ ID NO:5:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TCAGTGCTTT TCGAAGTACG CTTTGCTTTC TTTCACTCCA GGTTTGATTG CTTCAGATCC       60

TGGCTGCCAA TTGGCCGGAC ATACTTCACC GTGATTGTCG ACAAATTGAA AAGCTTGAAT      120

CAGACGTAAA GTTTCATCTA CAGAACGACC AACTGGAAGA TCATTGATTG TGATTTGTCG      180

CAAAATCCCT TTTGGATCAA TGATGAATAA TCCACGGTAA GCAATGCCAT CATCTTCCTT      240

GAGCACGCCA TATGCCCTAC TAATTGTATG ATTGGTATCA GCAAGAATTG GTATATTCAT      300

CTGACCGAGT CCACCCATTT TTCGGTCGGT ATTTACCCAT GCAAGGTGTG AAAAATGTGA      360

ATCAGTTGAG CATGCCATAA CAGCTACATC TAATTTTTTG AACTCCGCAA TACGATCAGA      420

AAAAGCAATT ATCTCTGTTG GGCAAACGAA AGTGAAATCG AGAGGATAAA AGAAGAGGAC      480
```

```
CACATATTTT CCTTTGAACT GACAAAGTGA AATTTCCTTG AAATCGCCAT TCACAACCGC      540

TGTTGTTTTG AAATTAGGGG CCGGTTGACC AATGAATGCT TTGCTTCCAG CAAGAGTCAT      600
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:6:

```
GGATCCCATG ACTCTTGCTG G                                                21
```

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:7:

```
GAATTCTCAG TGCTTTTCGA AGTACGC                                          27
```

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:8:

```
CCTCTCGATT TCACTTTCGT TTGCCCAACA GAGATA                                36
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:9:

```
GTAATACGAC TCACTATAGG GC                                               22
```

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: probe (xi) SEQUENCE DESCRIPTION: SEQ ID NO:10:

```
CATCTACAGA ACGACCAACT G                                                21
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated antibody that selectively binds to a protein encoded by a *Dirofilaria immitis* nucleic acid molecule that hybridizes to the nucleic acid sequence selected from the group consisting of SEQ ID NO:3 and SEQ ID NO:5 under conditions comprising (a) hybridizing in a solution comprising 2×SSC and 0% formamide, at a temperature of 37° C., and (b) washing in 1×SSC and 0% formamide at a temperature of 54° C.

2. The antibody of claim 1, wherein said nucleic acid molecule comprises a nucleic acid sequence selected from the group consisting of SEQ ID NO:1 and SEQ ID NO:4.

3. The antibody of claim 1, wherein said protein is encoded by a nucleic acid molecule comprising nDiTSA$_{600}$.

4. The antibody of claim 1, wherein said protein comprises an amino acid sequence that is at least about 80% identical to the amino acid sequence of SEQ ID NO:2.

5. The antibody of claim 1, wherein said protein comprises the amino acid sequence SEQ ID NO:2.

6. The antibody of claim 1, wherein said protein has thiol specific antioxidant activity.

7. A composition comprising an excipient and an isolated antibody that selectively binds to a protein encoded by a *Dirofilaria immitis* nucleic acid molecule that hybridizes to the nucleic acid sequence selected from the group consisting of SEQ ID NO:3 and SEQ ID NO:5 under conditions comprising (a) hybridizing in a solution comprising 2×SSC and 0% formamide, at a temperature of 37° C., and (b) washing in 1×SSC and 0% formamide at a temperature of 54° C.

8. The composition of claim 7, wherein said nucleic acid molecule comprises a nucleic acid sequence selected from the group consisting of SEQ ID NO: 1 and SEQ ID NO:4.

9. The composition of claim 7, wherein said protein is encoded by a nucleic acid molecule comprising nDiTSA$_{600}$.

10. The composition of claim 7, wherein said protein comprises an amino acid sequence that is at least about 80% identical to the amino acid sequence of SEQ ID NO:2.

11. The composition of claim 7, wherein said protein comprises amino acid sequence SEQ ID NO:2.

* * * * *